United States Patent [19]

Boigegrain et al.

[11] Patent Number: 5,159,103

[45] Date of Patent: Oct. 27, 1992

[54] 2-AMINO-7-HYDROXYTETRALINE ETHERS

[75] Inventors: Robert Boigegrain, Castelnau le Lez, France; Roberto Cecchi, Lodi-Milano; Sergio Boveri, Tortona, both of Italy

[73] Assignee: Sanofi, Paris, France

[21] Appl. No.: 825,841

[22] Filed: Jan. 28, 1992

Related U.S. Application Data

[63] Continuation of Ser. No. 365,853, Jun. 13, 1989, abandoned.

[30] Foreign Application Priority Data

Jun. 14, 1988 [FR]  France .................. 88 07948

[51] Int. Cl.⁵ .......................................... C07C 229/00
[52] U.S. Cl. ..................... 560/45; 562/452; 564/272; 564/327; 564/344
[58] Field of Search ................. 560/45; 562/452; 564/272, 327, 344

[56] References Cited

U.S. PATENT DOCUMENTS 4,921,998  5/1990  Niewohner .................. 560/45

Primary Examiner—Paul J. Killos
Attorney, Agent, or Firm—Bacon & Thomas

[57] ABSTRACT 2-amino-7-hydroxytetraline ethers of formula

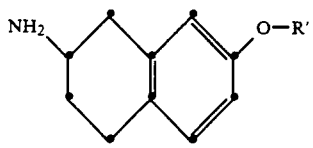

wherein R' represents methyl substituted by a carboxy group or lower carbalkoxy group or a salt thereof; a process for their preparation starting from the 2-amino-7-hydroxytetraline, N-protection, O-alkylation and N-deprotection; N-protected intermediates; and use of the compounds I for the preparation of the corresponding phenylethanolaminotetralines.

6 Claims, No Drawings

2-AMINO-7-HYDROXYTETRALINE ETHERS

This application is a continuation of application Ser. No. 07/365,853, filed Jun. 13, 1989, now abandoned.

The present invention concerns 2-amino-7-hydroxytetraline ethers, a process and intermediates for their preparation and their use for the synthesis of pharmacologically active phenylethanolaminotetralines.

The European patent Specification 211721 discloses phenylethanolaminotetralines of formula

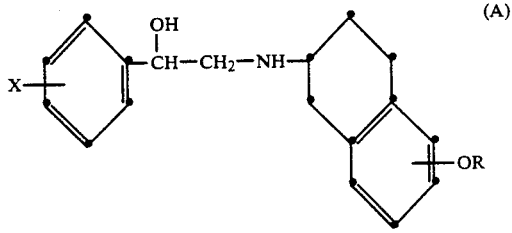

wherein X is hydrogen, halogen, a trifluoromethyl group or a lower alkyl group and R is hydrogen; a lower alkyl group unsubstituted or substituted by a cycloalkyl group of from 3 to 7 carbon atoms, a hydroxy group, a lower alkoxy, carboxy or lower carbalkoxy group; a cycloalkyl group of from 3 to 7 carbon atoms; or a lower alkanoyl group and their pharmaceutically acceptable salts.

According to this document, these compounds have interesting pharmacological properties, the compounds bearing the OR substituent in 7-position of the tetraline ring having shown a particularly pronounced lipolytic activity.

In the present description:
- the term "lower alkyl", designates a monovalent radical of a saturated hydrocarbon of from 1 to 4 carbon atoms, such as methyl, ethyl, propyl, isopropyl or n-butyl;
- the term "lower carbalkoxy", designates the carboxy group esterified with a lower alkyl as defined hereinabove;
- the term "halogen" includes the four halogens fluorine, chlorine, bromine, iodine, the first three ones being particularly preferred;
- the terms "tetraline" and "tetralone" refer to 1,2,3,4-tetrahydronaphtalene.

According to the above European patent specification, the products of formula (A) are prepared following different methods, always involving the reaction of a 2-aminotetraline or a 2-oxotetraline with
- a phenylethanolamine or
- a styrene epoxide or
- a phenylgloxal or
- an alpha-haloacetophenone.

Among the methods for the preparation of the products of formula (A) above, there is described an O-alkylation that, starting from 2-[(7-hydroxy-1,2,3,4-tetrahydronaphth-2-yl)amino]-1-phenylethanol or from 2-[(7-hydroxy-1,2,3,4-tetrahydronaphth-2-yl)amino]-1-(3-chlorophenyl)ethanol, by reaction with ethyl bromoacetate gives the 2-[(7-carbethoxymethoxy-1,2,3,4-tetrahydronaphth-2-yl)-amino]-1-phenylethanol, hereinafter designated COMPOUND 1, or the 2-[(7-carbethoxymethoxy-1,2,3,4-tetrahydronaphth-2-yl)-amino]-1-(3-chlorophenyl)ethanol, hereinafter designated COMPOUND 2. This reaction does not actually give good results because of the very low yield in final product.

These two products possess a very potent and selective activity on the intestinal motility, COMPOUND 2 being particularly interesting (Digestive Diseases and Sciences, 1987, 32, 907).

The European patent application EP 253 257 indicates, in a general formula, aminotetralines of formula

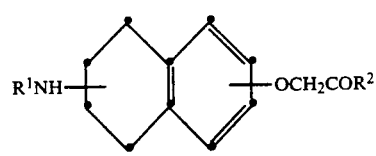

and, in a general formula again, aminotetralines intermediates of formula

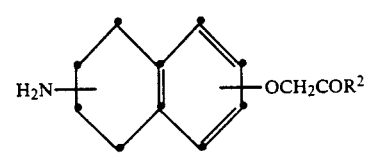

In formulas (B) and (C), $R^2$ represents, among others, OH or O-Alkyl.

The above document describes a series of aminotetraline O-ethers (C), but not the derivatives which are substituted in 2- and 7-positions, which among the products included in formula (A), especially in the case of COMPOUND 1 and COMPOUND 2, are particularly interesting.

It has now been found that, starting from a 2-amino-7-hydroxytetraline in which the amino group is protected by a group liable of being removed by catalytic hydrogenation or by mild acid hydrolysis, it is possible, by O-alkylation and N-deprotection, to prepare the 2-amino-7-hydroxytetraline etherified by a methyl group substituted by a carboxy group or by a lower carbalkoxy group.

It has also been found that by using the above mentioned protecting groups, it is possible to remove them, after the O-alkylation, without hydrolysing the lower carbalkoxy groups, thus obtaining the corresponding free aminotetraline.

It has finally been found that the 2-amino-7-hydroxytetraline etherified by a methyl group substituted by a carboxy or a lower carbalkoxy group may be used for the preparation of the corresponding phenylethanolaminotetralines, particularly COMPOUND 1 and COMPOUND 2 hereinabove, either by reaction with a styrene epoxide or by reaction with a mandelic acid and reduction of the mandelamide thus obtained.

Thus, the present invention concerns, according to one of its aspects, 2-amino-7-hydroxytetraline ethers of formula

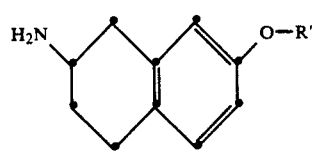

wherein R' represents a methyl group substituted by a carboxy or lower carbalkoxy group, and their salts.

The preferred lower carbalkoxy group is the carbethoxy group.

According to another of its aspects, the present invention concerns a process for the preparation of compounds I and of their salts, which comprises treating a N-protected 2-amino-7-hydroxytetraline of formula

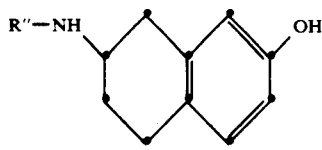

wherein R" represents a N-protecting group liable of being eliminated by catalytic hydrogenation or by mild acid hydrolysis, with a compound of formula R'-Hal      III wherein R' is as defined above and Hal is chlorine, bromine or iodine, in the presence of a basic condensing agent, submitting the N-protected 2-amino-7-hydroxytetraline ether thus obtained of formula

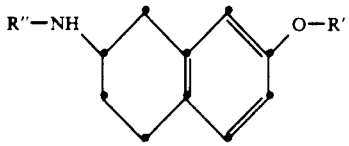

wherein R' and R" are as defined above, to a N-deprotection by catalytic hydrogenation or by mild acid hydrolisis and, after having, if desired, transformed the lower carbalkoxy group into carboxy group by saponification, isolating the product of formula I, as free base or amino acid or in the form of a salt, and, if desired, transforming the product thus obtained into one of its salts.

The preferred N-protecting groups R" are the tert-butoxycarbonyl (Boc), benzyloxycarbonyl groups and, generally, the N-protecting groups used in the peptide chemistry or the benzyl, benzhydryl or trityl group, non substituted or substituted with a methoxy group on the phenyl radical or one of the phenyl radicals.

As a compound of formula III, a lower alkyl bromoacetate is preferably used, methyl or ethyl bromoacetate being particularly preferred. The reaction is carried out in an organic solvent, such as acetone, ethyl acetate or tetrahydrofuran by employing a classical basic condensing agent, such as an alkali metal carbonate, for example potassium carbonate.

The ether of the N-protected 2-amino-7-hydroxytetraline IV thus obtained is isolated according to the conventional methods, optionally in the form of one of its salts and subjected to N-deprotection.

The removal of the N-protecting groups is carried out by catalytic hydrogenation or by mild acid hydrolisis according to well known methods of the literature. Particularly, the Boc group is removed under acid conditions, by treatment with trifluoroacetic or hydrochloric acid. The other N-protecting groups are removed by catalytic hydrogenation, preferably by utilizing palladium on charcoal as a catalyst. The trityl and methoxytrityl groups may also be hydrolysed under mild acid conditions, for example by utilizing 50% formic acid or hydrogen chloride in an organic solvent.

The compounds of formula I wherein R' represents methyl substituted by a lower carbalkoxy group may be subjected to a saponification to obtain the corresponding carboxy group, either before or after the deprotection of the amino group.

The products I are isolated according to conventional methods, preferably in the form of one of their salts. The free base may be obtained by neutralization and transformed into another salt. When in the product of formula I R' is methyl substituted by a carboxy group, the resulting aminoacid may be transformed into an acid addition salt or into a salt with a metal, particularly alkaline metal, such as the sodium salt.

The N-protected 2-amino-7-hydroxytetraline of formula II is prepared either starting from the 2-amino-7-hydroxytetraline of formula IIa

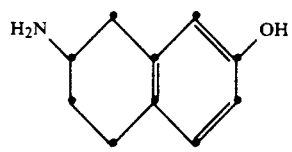

or directly starting from the 7-methoxy-2-tetralone of formula V

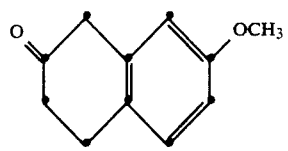

without passing through the 2-amino-7-hydroxytetraline IIa.

The 2-amino-7-hydroxytetraline IIa is prepared starting from the corresponding methoxytetralone of formula V by reaction with benzylamine, reduction of the benzylimine so obtained with sodium borohydride, debenzylation by catalytic hydrogenation and demethylation by 48% hydrobromic acid, according to the following Scheme 1

SCHEME 1

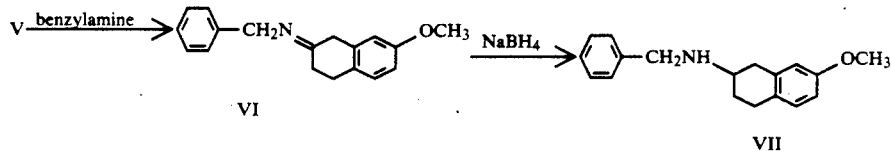

-continued
SCHEME 1

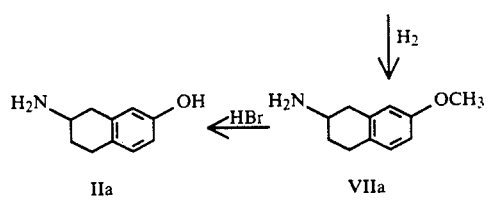

IIa    VIIa

The reaction of product V with benzylamine is carried out according to the classical methods for the preparation of Schiff bases, in an organic solvent such as toluene in the presence of p-toluenesulfonic acid and compound VI thus obtained may be reduced, without isolation and purification, with sodium borohydride. By catalytic hydrogenation, using for example palladium on charcoal, the 2-amino-7-methoxytetraline VIIa is obtained, that, by heating in 48% hydrobromic acid, gives the 2-amino-7-hydroxytetraline IIa, as hydrobromide, converted into the free base by neutralisation.

In the step V→VI, benzylamine may be replaced by tritylamine or benzhydrylamine, these three products being optionally substituted by a methoxy group on the phenyl radical or one of the phenyl radicals.

The two optically active forms of the aminotetralines of formula IIa, VII and VIIa are prepared by resolving the racemate according to known methods, for example by salification with an optically active acid, preferably mandelic acid.

The N-protection with the R" group is carried out by reacting a compound of formula IIa with the suitable reagent for the protection of the amino groups as described, for example, by M. Bodanszky et al., Peptide Synthesis, 2nd Edition, John Wiley & Sons 1976, pages 18 to 49, chapters 3 to 6.

The Boc group, for example, may be introduced by reaction with the di-tert-butyldicarbonate in a basic medium. The benzyloxycarbonyl group may be introduced according to the general procedure described by E. C. Horning, Organic Synthesis, vol. III, Wiley, New York 1955, page 167.

Thus, for example, the products I may be prepared by protecting the amino group of the 2-amino-7-hydroxytetraline IIa with a Boc group by reaction with di-tert-butyldicarbonate in an organic solvent such as dioxane or dimethylformamide, treating the product thus obtained with a compound of formula III in an alkaline medium and by deprotecting the amino group by eliminating the Boc group with trifluoroacetic or hydrochloric acid according to the following Scheme 2

SCHEME 2

IIa⟶

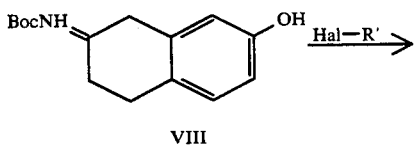

VIII

-continued
SCHEME 2

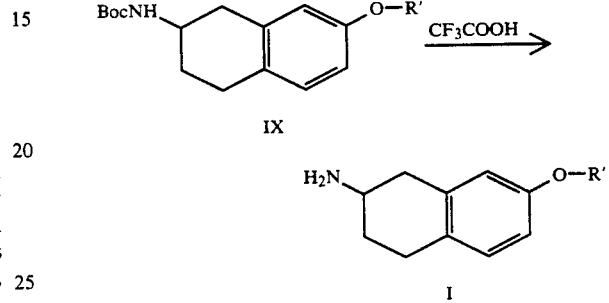

IX

I

The preparation of the amine I by the removal of N-protecting Boc group does not involve any modification of the lower carbalkoxy group or of the stereoconfiguration.

The N-protection may be also carried out starting from the 7-methoxy-2-tetralone V, without passing through the 2-amino-7-hydroxytetraline IIa, by forming a Schiff base with an amine selected from the group of benzylamine, benzhydrylamine and tritylamine, non substituted or substituted by a methoxy group on the phenyl or one of the phenyl radicals and reduction with sodium borohydride.

Thus, for example, products I may be prepared starting from 2-benzylamino-7-methoxytetraline of formula VII (Scheme 1), by demethylation with hydrobromic acid, reaction of the corresponding phenol with a compound of formula III in an alkaline medium and debenzylation, according to the following Scheme 3

SCHEME 3

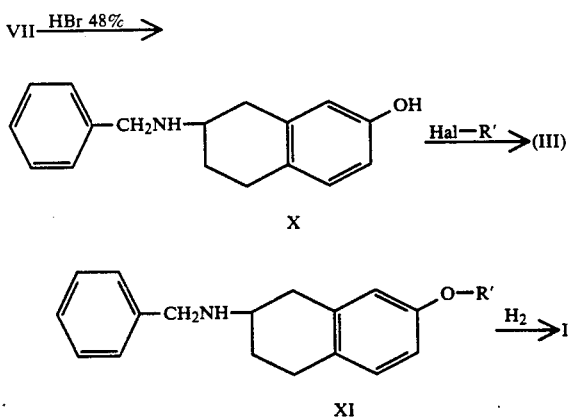

In Scheme 2 above, the Boc group may be substituted by the benzyloxycarbonyl group or by any other protecting group as defined above. In Scheme 3 the benzyl group may be substituted on the phenyl radical by a methoxy group or may be replaced by a benzhydryl or trityl group, non substituted or substituted on one of the phenyl radicals by a methoxy group. The deprotection is carried out as indicated above.

The ethers of the N-protected 2-amino-7-hydroxytetraline IV and their possible salts are novel intermediates, those wherein the substituent R' is (lower carbalkoxy)methyl, for example carbomethoxymethyl or carbethoxymethyl, being particularly preferred.

These products, in their racemic form or in the form of their stereoisomers, represent another aspect of the present invention.

According to a further aspect, the present invention concerns the use of 2-amino-7-hydroxytetraline ethers of formula I for the preparation of the corresponding phenylethanolaminotetralines of formula XII

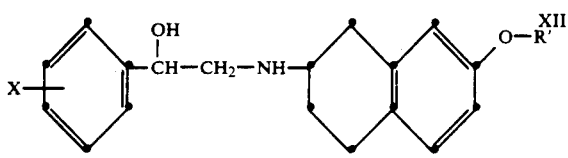

wherein X and R' are as defined above, and their pharmaceutically acceptables salts.

Said use involves both a reaction of compounds I with a styrene epoxide of formula

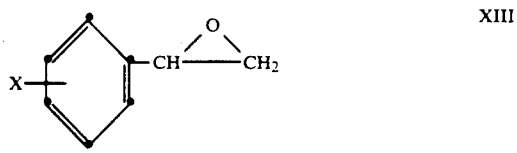

wherein X is as defined above, said styrene epoxide being either racemic or, particularly when X is hydrogen or 3-chloro, optically active, and a reaction with a functional derivative of a mandelic acid of formula

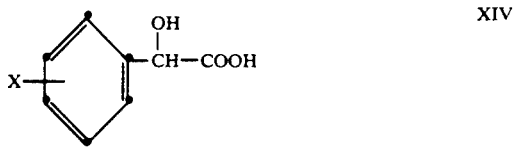

wherein X is as defined above and a reduction of the amidic carbonyl group of the mandelamide thus obtained of formula

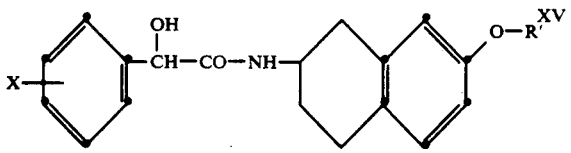

wherein X and R' are as defined above, to a methylene group, said mandelic acid XIV being either racemic or, particularly when X is hydrogen or 3-chloro, optically active, and a possible salification.

The following examples illustrate the invention without however limiting it. Unless otherwise specified, the specific optical rotatory symbol is indicates as /alpha/, but it must be read $[alpha]_D^{20}$.

PREPARATION I 2-amino-7-hydroxytetraline hydrobromide (a) A mixture of 8 g of 7-methoxy-2-tetralone, 4.8 g of benzylamine, 150 ml of anhydrous toluene and 100 mg of p.toluenesulfonic acid is refluxed for three hours. The mixture is evaporated to dryness, the oily residue is taken up with 100 ml of methanol and to the solution thus obtained 8.5 g of sodium borohydride are cautiously added at 0°-5° C. The mixture is left under stirring at room temperature for a night, then added with 50 ml of water and left under stirring for 30 minutes. The solvent is evapored, the residue is taken up with 30 ml of water and 10 ml of a concentrated solution of ammonium hydroxide. After extraction with 200 ml of ethyl acetate, the organic phase is dried over sodium sulfate, filtered and evaporated to dryness. A dark coloured oil is obtained, which is purified by flash chromatography using a mixture ethyl acetate/methanol 95/5 as an eluent. The base so obtained is converted into its hydrochloride by solution in 40 ml of isopropanol and addition of isopropanol saturated with hydrogen chloride to give 11.4 g of 2-benzylamino-7-methoxytetraline hydrochloride; m.p. 265°-267° C. (dec.).

(b) The product above, dissolved in 200 ml of methanol and 100 ml of water, is hydrogenated in the presence of 1.2 g of 10% palladium on charcoal under room pressure and at 45°-50° C. After 4 hours the mixture is filtered, evaporated to dryness, taken up twice with absolute ethanol and evaporated to dryness. A white solid is obtained which is taken up with 70 ml of hot isopropanol. By cooling, the suspension so obtained precipitates and gives 7.8 g of 2-amino-7-methoxytetraline hydrochloride; m.p. 214°-216° C.

(c) A suspension of 6.6 g of the above product in 80 ml of 48% hydrobromic acid is heated under reflux for 2 hours. The resulting solution is evaporated to dryness, taken up with absolute ethanol and evaporated twice to dryness. The oil so obtained is dissolved in 20 ml of hot isopropanol. By adding 30 ml of ethyl ether to the solution, 6.8 g of crystalline 2-amino-7-hydroxytetraline hydrobromide are obtained; m.p. 171°-173° C.

PREPARATION II (R)-2-amino-7-hydroxytetraline monohydrate

To a solution in 550 ml of absolute ethanol of 50 g of 2-amino-7-methoxytetraline crude base, obtained from the corresponding hydrochloride (PREPARATION I b) by neutralisation with 10% sodium hydroxide, extraction with ethyl acetate and evaporation of the solvent, there is added a solution of 43 g of (+) mandelic acid in 550 ml of absolute ethanol. After a night at room temperature, the precipitate is filtered and crystallized twice from absolute ethanol by recovering every time the product which cristallyzes after a night at room temperature. Thus, 34.2 g (74%) of the pure salt of the (+) mandelic acid with (+)-2-amino-7-methoxytetraline are obtained; m.p. 190°-192° C. The mother-liquors of this first crystallization are separated and used for PREPARATION III hereinbelow. A suspension of 34 g of the salt thus obtained in 300 ml of water is made basic with N sodium hydroxide. The base is extracted with ethyl acetate, evaporated to dryness and the residue is taken up with 260 ml of 48% hydrobromic acid. The mixture is heated under reflux for three hours, evaporated to dryness under vacuum and the residue so obtained is taken up with 70 ml of water. The aqueous solution is made basic with concentrated ammonium hydroxide, cooled during a night and filtered. Thus, 17 g of (R)-2-amino-7-hydroxytetraline monohydrate are obtained; m.p. 143°-144° C., /alpha/= +85.1° (methanol, c=0.5%). The hydrochloride of this product has an optical rotation corresponding to that of the literature (Molecular Pharmacology, 1982, 22, 281-289).

PREPARATION III (S)-2-amino-7-hydroxytetraline monohydrate

The mother-liquors of the first crystalization saved in PREPARATION II are evaporated to dryness, the residue so obtained is suspended in 300 ml of water and the solution is made basic with N sodium hydroxide. The base is extracted with ethyl acetate. By following the method described in PREPARATION II and using the base so obtained and the (−) mandelic acid as starting products, the salt of the (−) mandelic acid with (−)-2-amino-7-methoxytetraline (m.p. 189°-191° C.) is obtained, which by neutralization and demethylation with hydrobromic acid, gives 17 g of (S)-2-amino-7-hydroxytetraline, in the form of monohydrate; m.p. 143°-144° C., /alpha/= −86.9° (methanol, c=0.5%). The hydrochloride of this product has an optical rotation corresponding to that of the literature (Molecular Pharmacology 1982, 22, 281-289).

PREPARATION IV (S)-2-benzylamino-7-hydroxytetraline hydrobromide (a) To a solution of 44 g of 2-benzylamino-7-methoxytetraline base, obtained by neutralization of the hydrochloride described in PREPARATION I (a), in 140 ml of absolute ethanol, there is added a solution of 24.5 g of (−)-mandelic acid in 150 ml of absolute ethanol. After a night at room temperature, the salt which crystallizes is filtered and washed with ethyl ether. There is obtained 42 g of a product having a m.p. of 150°-152° C. and a [alpha]$_{365}^{20}$ of −267° (methanol, c=1%) which, after crystallization, affords 33 g of (−)-mandelic salt; m.p. 155°-157° C., [alpha]$_{365}^{20}$= −316° (methanol, c=1%). A solution of 30 g of the obtained salt in 400 ml of water is neutralized with 32% ammonium hydroxide and the mixture is extracted with ethyl acetate. The organic phase is washed with water, dried over sodium sulfate and evaporated. There is obtained the (S)-2-benzylamino-7-methoxytetraline base as an oil which is dissolved in isopropanol and treated with a solution of HCl in isopropanol. The precipitated hydrochloride is filtered and dried to give 22 g of product; m.p. 287°-290° C. By crystallization of 1 g of this product in a mixture methanol/water 1/1 there is obtained 0.8 g of (S)-2-benzylamino-7-methoxytetraline hydrochloride; m.p. 287°-290° C., [alpha]$_{365}^{20}$= −231° (methanol, c=1%).

(b) A suspension of 15 g of the product so obtained in 100 ml of 48% hydrobromic acid and 100 ml of 33% hydrobromic acid in acetic acid is heated at reflux and the resulting solution is evaporated to dryness. The residue is taken up with absolute ethanol, this operation being repeated twice again. The oily residue is dissolved in acetone and crystallized. Then the product is filtered, washed first with acetone, then with ethyl ether and dried. Thus, 17 g of (S)-2-benzylamino-7-hydroxytetraline hydrobromide are obtained; m.p. 185°-187° C.; [alpha]$_{365}^{20}$= −200° (methanol, c=1%).

EXAMPLE 1

2-benzylamino-7-carbethoxymethoxytetraline hydrochloride (a) A mixture of 25 g of 2-benzylamino-7-methoxytetraline hydrochloride, PREPARATION I (a), in 215 ml of a 33% hydrobromic acid solution in acetic acid and in the presence of 36 ml of 48% hydrobromic acid, is heated at reflux for 2 hours under stirring. After concentration under reduced pressure, the residue is taken up three times with 100 ml of absolute ethanol and dried every time. The product thus obtained is triturated with 150 ml of acetone, the mixture is filtered to give 25.3 g of 2-benzylamino-7-hydroxytetraline hydrobromide; m.p. 198°-200° C. The salt is dissolved in 1300 ml of hot water and, after cooling, there is added a concentrated ammonium hydroxide solution. The base is extracted with ethyl acetate, dried and a solid is obtained which after crystallization from 250 ml of toluene gives 14 g of 2-benzylamino-7-hydroxytetraline base; m.p. 161°-163° C.

(b) A mixture of 23 g of 2-benzylamino-7-hydroxytetraline base (a) and 4.5 g of 55% sodium hydride in 800 ml of toluene is heated at 70° C. under nitrogen for 30 minutes. A mixture of 15.2 g of ethyl bromoacetate and 0.5 g of tetrabutylammonium bromide in 200 ml of toluene is added dropwise thereto at room temperature, then the reacting mixture is heated for 3 hours at 70° C. and cooled. After addition of 100 ml of water the organic phase is separated, washed with water, dried and concentrated to give 31 g of an oil which is dissolved in isopropanol. After addition of a solution of isopropanol satured with hydrogen chloride, 28 g of 2-benzylamino-7-carbethoxymethoxytetraline hydrochloride are obtained; m.p. 188°-190° C.

EXAMPLE 2

2-amino-7-carbethoxymethoxytetraline hydrochloride

A solution of 27 g of 2-benzylamino-7-carbethoxymethoxytetraline hydrochloride, EXAMPLE 1, in 300 ml of 95% ethanol and 25 ml of water, is hydrogenated under ordinary pressure and at temperature of 50° C. by using 3 g of 10% palladium on charcoal as a catalyst. After 3 hours, the mixture is filtered, the residue is taken up twice with 100 ml of absolute ethanol and dried every time. The product so obtained is triturated in 150 ml of acetone, filtered and crystallized from 100 ml of isopropanol to give 19 g of 2-amino-7-carbethoxymethoxytetraline hydrochloride; m.p. 143°-145° C. The product thus obtained may be used for the preparation of the compound of formula (XV) above, in which X is hydrogen and O-R' is a carbethoxymethoxy group (COMPOUND 1), as follows: A solution of 1.8 g of phenyloxirane and 3.7 g of 2-amino-7-carbethoxymethoxytetraline base, obtained by neutralization of the hydrochloride described above, in 40 ml of n-butanol is heated under reflux for 6 hours. The mixture is concentrated to dryness, the residue is purified by flash chromatography, by eluting with a mixture of ethyl acetate/methanol 9/1. The purified oil is left to react overnight with an excess of oxalic acid in 5 ml of isopropanol. Thus, 1.9 g of N-(7-carbethoxymethoxy-1,2,3,4-tetrahydronaphth-2-yl)-2-hydroxy-2-phenylethanamine oxalate is obtained; m.p. 159°-162° C., identical with the compound of Example 5 of the European patent 211 721.

EXAMPLE 3

(R)-2-tert-butoxycarbonylamino-7-carbethoxymethoxytetraline (a) A solution of 5.4 g of (R)-2-amino-7-hydroxytetraline monohydrate, PREPARATION II, in 40 ml of dimethylformamide and in the presence of 15 g of triethylamine is heated under stirring at 40° C. The mixture thus obtained is cooled to 20° C. and 7.2 g of di-tert-butyldicarbonate are added thereto. The reacting mixture is left under stirring for 3 hours at room temperature, then added with 100 ml of water and extracted with 240 ml of ethyl ether. The organic phase in washed with water, dried over sodium sulfate and evaporated to dryness. Thus, 10.8 g of (R)-2-tert-butoxycarbonylamino-7-hydroxytetraline are obtained as an oily product.

(b) A solution of 10.8 g of (R)-2-tert-butoxycarbonylamino-7-hydroxytetraline (a) in 300 ml of acetone, is heated at reflux under stirring for 6 hours in the presence of 12.4 g of powdered anhydrous potassium carbonate and 15.1 g of ethyl bromoacetate. After filtration, acetone is evaporated under reduce pressure and the residue is taken up with ethyl ether. The solution so obtained is washed with water, dried over sodium sulfate and evaporated to dryness. The residue is taken up with ethyl ether and crystallized from isopropyl ether. Thus, 4.8 g of (R)-2-tert-butoxycarbonylamino-7-carbethoxymethoxytetraline are obtained; m.p. 113°–115° C., /alpha/= +57.97° (methanol, c=1%).

EXAMPLE 4

(R)-2-amino-7-carbethoxymethoxytetraline hydrochloride (a) A solution of 3.5 g of (R)-2-tert-butoxycarbonylamino-7-carbethoxymethoxytetraline, EXAMPLE 3, in 35 ml of methylene chloride is cooled to 0° C. Then, there is added a solution of 7.7 ml of trifluoroacetic acid in 40 ml of methylene chloride and the mixture is left to stand under stirring at first 30 minutes at a temperature of 0°–5° C., then 4 hours at room temperature. After neutralization with a solution of sodium bicarbonate, the organic phase is separated, washed with water, dried and evaporated to dryness. The residue is taken up with 15 ml of ethyl acetate and made acid with a solution of hydrochloric acid in ethanol. The precipitated so obtained is filtered and washed with ether. Thus, 1.1 g of (R)-2-amino-7-carbethoxymethoxytetraline hydrochloride is obtained; m.p. 168°–171° C., /alpha/= +51.14° (methanol, c=1%). (b) To a solution of 5.8 g of (R)-2-tert-butoxycarbonylamino-7-carbethoxymethoxytetraline, EXAMPLE 3, in 135 ml of absolute ethanol there is added at room temperature 82 ml of a 7.2N solution of hydrogen chloride in ethanol. The mixture is left under stirring at room temperature for 150 minutes, then it is evaporated to dryness under reduced pressure. The residue is taken up with ethyl ether and filtered. Thus, 4.6 g of (R)-2-amino-7-carbethoxymethoxytetraline hydrochloride are obtained; m.p. 170°–171° C., /alpha/= +51° (methanol, c=1%). By crystallization from methanol, the melting point remains unchanged (170°–172° C.) and the /alpha/ rises to +51.6° (methanol, c=1%).

EXAMPLE 5

(S)-2-tert-butoxycarbonylamino-7-carbethoxymethoxytetraline (a) A solution of 5.4 g of (S)-2-amino-7-hydroxytetraline monohydrate, PREPARATION III, in 40 ml of dimethylformamide is heated at 40° C. under stirring in the presence of 15 g of triethylamine. The mixture thus obtained is cooled to 20° C. and added with 7.2 g of di-tert-butyldicarbonate. By following the procedure described in EXAMPLE 3(a), the (S)-2-tert-butoxycarbonylamino-7-hydroxytetraline is obtained, which is directly used for the following step. (b) The (S)-2-tert-butoxycarbonylamino-7-hydroxytetraline obtained in (a) is dissolved in 300 ml of acetone. By operating as described in EXAMPLE 3(b) the (S)-2-tert-butoxycarbonylamino-7-carbethoxymethoxytetraline is obtained; /alpha/= −59° (methanol, c=1%).

EXAMPLE 6

(S)-2-amino-7-carbethoxymethoxytetraline hydrochloride.

A solution of 1 g of (S)-2-[N-(tert-butoxycarbonyl)amino]-7-carbethoxymethoxytetraline, EXAMPLE 5, in 15 ml of methylene chloride is cooled to 0° C. A solution of 2.2 ml of trifluoroacetic acid in 15 ml of methylene chloride is added thereto and the reacting mixture is left under stirring 30 minutes at a temperature of 0°–5° C. and afterwards 4 hours at room temperature. By operating as described in EXAMPLE 4, the (S)-2-amino-7-carbethoxymethoxytetraline hydrochloride is obtained; /alpha/= −52° (methanol, c=1%).

The product so obtained may be used for the preparation of N-[(2S)-7-carbethoxymethoxy-1,2,3,4-tetrahydronaphth-2-yl]-(2R)-2-hydroxy-2-phenylethanamine (R,S isomer of COMPOUND 1) as follows: (a) To a suspension of 5.7 g of (S)-2-amino-7-carbethoxymethoxytetraline hydrochloride, 3 g of (R)-mandelic acid and 8 g of benzotriazolyl-N-oxytris(dimethylamino)phosphonium hexafluorophosphate (BOP) in 100 ml of anhydrous methylene chloride, there is slowly added 5.6 ml of triethylamine, then the solution thus obtained is left under stirring at room temperature for 5 hours. After addition of 150 ml of a saturated solution of sodium chloride, the mixture is left under stirring for 30 minutes at room temperature, added with 500 ml of ethyl acetate. The organic phase is washed at first with a 1N solution of hydrochloric acid, then with a saturated solution of sodium bicarbonate and sodium chloride. The organic solution is dried on sodium sulfate, filtered and evaporated to dryness. The oil thus obtained is purified by flash chromatography by using a mixture of ethyl acetate/cyclohexane 55/45 as a solvent. The resulting solid is triturated in 20 ml of ethyl ether and the product thus obtained is crystallized from ethyl acetate to give N-[(2S)-7-carbethoxymethoxy-1,2,3,4-tetrahydronaphth-2-yl]-(R)-mandelamide; m.p. 115°–117° C.; /alpha/= −98.3° (methanol, c=1%). Yield: 55%. (b) To a solution of 5 g of N-[(2S)-7-carbethoxymethoxy-1,2,3,4-tetrahydronaphth-2-yl]-(R)-mandelamide in 50 ml of anhydrous tetrahydrofuran, 2.6 ml of a 10M solution of boranemethylsulfide (diborane generating reagent consisting of a complex of borane and dimethylsulfide) in 10 ml of anhydrous tetrahydrofuran are added drop by drop during 10 minutes under nitrogen at a temperature of 0° C. The mixture is left to stand overnight at room temperature. The unreacted boranemethylsulfide is destroyed by cautiously adding 30 ml of absolute ethanol and heating at reflux for 30 minutes. After evaporation to dryness a flash chromatography is carried out by eluting with a mixture of ethyl acetate/methanol 85/15. Two products separate which are taken up with ethyl ether. The less polar product gives, after crystallization from ethyl acetate, 1.2 g of N-[(2S)-7-carbethoxymethoxy-1,2,3,4-tetrahydronaphth-2-yl]-(2R)-2-hydroxy-2-phenylethanamine; m.p. 108°–111° C.; /alpha/=−78.65° (methanol, c=1%). The more polar product gives, after crystallization from ethyl acetate, 0.5 g of N-[(2S)-7-(2-hydroxyethoxy-1,2,3,4-tetrahydronaphth-2-yl]-(2R)-2-hydroxy-2-phenylethanamine; m.p. 94°–96° C.; /alpha/=−83.68° (methanol, c=1%).

We claim:

1. A 2-amino-7-hydroxytetraline ether of formula

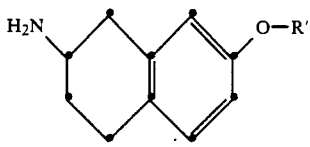

in which R' represents a methyl group substituted by a carboxy or lower carbalkoxy group, or a salt thereof.

2. A process for the preparation of a 2-amino-7-hydroxytetraline ether according to claim 1 which comprises treating a N-protected 2-amino-7-hydroxytetraline of formula

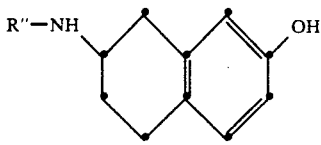

wherein R" represents a N-protecting group liable of being eliminated by catalytic hydrogenation or by mild acid hydrolysis, with a compound of formula R'-Hal        III wherein R' is as defined in claim 1 and Hal is chlorine, bromine or iodine, in the presence of a basic condensing agent, submitting the N-protected 2-amino-7-hydroxytetraline ether thus obtained of formula

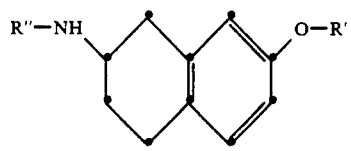

wherein R' and R" are as defined above, to a N-deprotection by catalytic hydrogenation or by mild acid hydrolysis and, after having, if desired, transformed the lower carbalkoxy group into carboxy group by saponification, isolating the product of formula I, as free base or amino acid or in the form of a salt, and, if desired, transforming the product thus obtained into one of its salts.

3. A process as claimed in claim 2 in which the N-protecting group is selected from the group consisting of tert-butoxycarbonyl, benzyloxycarbonyl or the benzyl, benzhydryl and trityl group unsubstituted or substituted by a methoxy group on the phenyl radical or one of the phenyl radicals.

4. The compound of claim 1 which is 2-amino-7-carbethoxymethoxy-1,2,3,4-tetrahydronaphtalene or a salt thereof.

5. The compound of claim which is (R)-2-amino-7-carbethoxymethoxy-1,2,3,4-tetrahydronaphtalene or a salt thereof.

6. The compound of claim 1 which is (S)-2-amino-7-carbethoxymethoxy-1,2,3,4-tetrahydronaphtalene or a salt thereof.

* * * * *